(12) United States Patent
Cartledge

(10) Patent No.: US 6,328,712 B1
(45) Date of Patent: *Dec. 11, 2001

(54) RAPID INFUSION SYSTEM

(75) Inventor: Richard G. Cartledge, Macon, GA (US)

(73) Assignee: Smisson-Cartledge Biomedical Corporation, Macon, GA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/172,512

(22) Filed: Oct. 14, 1998

Related U.S. Application Data (63) Continuation-in-part of application No. 08/608,291, filed on Feb. 28, 1996, now Pat. No. 5,840,068.

(51) Int. Cl.[7] ............................... A61F 7/12; A61M 1/00
(52) U.S. Cl. .................................. 604/113; 604/151
(58) Field of Search ................ 604/65, 66, 67, 604/113, 123, 131, 151

(56) References Cited

U.S. PATENT DOCUMENTS

| | | | |
|---|---|---|---|
| 3,985,133 | 10/1976 | Jenkins et al. ................ 128/214 |
| 4,012,177 | 3/1977 | Yakich ........................... 417/477 |
| 4,187,057 | 2/1980 | Xanthopoulos ................. 417/63 |
| 4,256,437 | 3/1981 | Brown ........................... 417/45 |
| 4,275,726 | * 6/1981 | Schael ....................... 604/67 X |
| 4,410,322 | 10/1983 | Archibald ..................... 604/153 |
| 4,475,901 | * 10/1984 | Kraegen et al. ............... 604/67 |
| 4,537,561 | 8/1985 | Xanthopoulos ................. 417/63 |
| 4,685,900 | 8/1987 | Edwards et al. ................ 604/153 |
| 4,747,826 | 5/1988 | Sassano .......................... 604/52 |
| 4,808,167 | * 2/1989 | Mann et al. .................. 604/151 |
| 4,856,972 | 8/1989 | Van Benschoten et al. ...... 417/477 |
| 4,950,136 | 8/1990 | Haas et al. .................... 417/477 |
| 5,061,241 | 10/1991 | Stephens, Jr. et al. .......... 604/114 |
| 5,104,374 | 4/1992 | Bishko et al. ................. 604/31 |
| 5,236,126 | 8/1993 | Desjardins .................... 248/214 |
| 5,308,333 | 5/1994 | Skakoon ....................... 604/126 |
| 5,366,346 | 11/1994 | Danby .......................... 417/18 |
| 5,385,540 | 1/1995 | Abbott et al. .................. 604/4 |
| 5,415,532 | 5/1995 | Loughnane et al. ............ 417/411 |
| 5,419,684 | 5/1995 | Struble et al. ................. 417/44.2 |
| 5,464,391 | * 11/1995 | DeVale ..................... 604/131 X |
| 5,482,446 | * 1/1996 | Williamson et al. . |
| 5,573,502 | * 11/1996 | LeCocq et al. ............. 604/151 X |
| 5,577,891 | 11/1996 | Loughnane et al. ............ 417/53 |
| 5,746,719 | * 5/1998 | Farra et al. ................... 604/151 |
| 5,755,691 | * 5/1998 | Hilborne ....................... 604/151 |
| 5,782,805 | * 7/1998 | Meinzer et al. ............. 604/151 X |
| 5,840,068 | * 11/1998 | Cartledge ...................... 604/131 |
| 5,928,196 | * 7/1999 | Johnson et al. ............ 604/151 X |

FOREIGN PATENT DOCUMENTS 0 120 284 A1    10/1984    (EP) .
WO 97/21456    6/1997    (WO) .

* cited by examiner

*Primary Examiner*—Jeffrey A. Smith
(74) *Attorney, Agent, or Firm*—Sutherland, Asbill & Brennan, LLP (57) ABSTRACT

A rapid infusion system for rapidly delivering blood and/or volume expanding fluid to a patient, said rapid infusion device comprising in combination: a portion which includes an adjustable drive mechanism and related control mechanism therefor, and a portion which includes components that come into contact with the fluid infused to the patient, and optionally wherein said system can be portable.

13 Claims, 5 Drawing Sheets

Fig_14

Fig_17

Fig_15

Fig_16

Fig_18

RAPID INFUSION SYSTEM

This application is a continuation in part of Ser. No. 08/608,291, filed Feb. 28, 1996, now issued as U.S. Pat. No. 5,840,068.

FIELD OF THE INVENTION

This invention relates to an apparatus for the rapid infusion of circulatory supportive fluids such as blood into a patient. The system comprises permanent and disposable components. The various components which physically come into contact with the fluid being infused can easily be removed and disposed. The principal advantage achieved from this arrangement resides in the fact that it is small, lightweight, and portable. The system can be of a size to fit in a person's hand and is ideal for use by emergency personnel.

BACKGROUND OF THE INVENTION

During surgery or in the emergency room, it is frequently necessary to infuse blood or volume expanding fluids rapidly into a patient, particularly when massive blood losses have occurred. Patients having inadequate blood volume can suffer serious consequences.

There are many situations where large amounts of blood can be lost in a very short period of time, for example, in cases of serious automobile accidents, gun shot wounds in critical areas of the body, and a variety of plural surgeries including cancer surgery and heart and liver transplants.

In the past, the replacement of large amounts of blood loss has been a major problem to the surgical teams attending a suffering patient. A common method of rapid infusion includes the use of a plurality of infusion sites simultaneously. Infusion bags or bags of stored banked blood are interconnected by intravenous tubing. Frequently, a plurality of medical personnel are required to oversee the various infusion sites and to personally ensure the flow of blood from the blood bags.

Anesthesiologists and/or other ancillary staff are regularly involved with cardiopulmonary resuscitation, trauma and organ transplantation procedures, and with maintenance of patient hemodynamics during any operative or emergency procedure. During such procedures, patient blood loss cannot, practically speaking, always be contained by the operating surgeon and such blood must be replaced by the anesthesiologists standing in attendance. It is not uncommon for multiple anesthesiologists or technicians to stand in attendance during lengthy operations attempting to infuse massive quantities of blood through five or six venous catheters.

Clinical records obtained from actual operations involving trauma and liver transplantations reveal blood losses estimated to be in excess of two hundred and fifty liters, a volume approximately fifty times a normal adult's total blood volume. Although it is not uncommon for an anesthesiologist or trauma surgeon to encounter massive exsanguination (ten liters and more) in a major trauma and transplantation center, it is, however, unusual to successfully resuscitate a patient with such massive blood volume loss with traditional methods.

Stephens, Jr., et al., U.S. Pat. No. 5,061,241, disclose a rapid infusion device capable of high volume pumping composed of two units. A permanent unit comprising a base portion which houses an AC/DC motor, a roller pump, and other associated gauges and switches. A disposable unit includes a filter reservoir, heat exchange component, and associated tubing leading to the roller pump. The roller pump increases the volume of fluid being pumped by increasing the rpm of the pumping unit and includes a pressure control valve.

Sassano, U.S. Pat. No. 4,747,826, discloses an infusion apparatus consisting of supply sources, reservoirs, and associated tubes and valves leading to an infusion pump which can either be a roller head occlusive or centrifugal pump.

The rapid infusion of IV fluids has proven to save lives in patients suffering from blood loss. All rapid infusion devices presently available are large, heavy, prohibitively expensive, and extremely costly to operate because of special, extremely expensive components that have to be discarded after each use. All of these devices are large, cumbersome, difficult to use, require specialized training, require long set up time, use specialized tubing, do not have their own power supply and are not suitable to ambulance or field use. The prior art rapid-infusion devices cannot be used with typical peripheral IV cannulas but require large-bore central-line or venous cut-down catheters which can be inserted only by physicians. Although rapid infusion, or hyperinfusion, is a proven life saver, this technology is not commonly available to the public in most hospitals because of the aforementioned reasons.

SUMMARY OF THE INVENTION

With knowledge of the shortcomings of present day blood infusion apparatuses noted above, applicant has developed the rapid infusion system disclosed and claimed in the instant application.

An object of the present invention is the provision of an apparatus which satisfies the various requirements of rapid infusion while at the same time reduces the number of medical and/or technical personnel required to monitor the equipment, a much desired improvement over presently known systems and practices used in critical, life threatening situations.

A further object of the present invention is to provide an adjustable system which is capable of high volume infusion of blood, blood components, oxygen-carrying substances, plasma, plasma components, contrast material, drugs, any physiological fluid, and/or volume expanding fluids, all of which are hereinafter referred to as "fluids," into a patient.

BRIEF DESCRIPTION OF THE DRAWINGS

Referring to the drawings.

DESCRIPTION OF THE PREFERRED EMBODIMENTS

The rapid infusion device of the present invention solves many problems present in prior art devices. It is small and portable, and if desired can be constructed so as to fit in the palm of the hand. It is inexpensive and thus can be made available to patients even in small rural hospitals. It can be used with any IV tubing or other commonly available hospital equipment and can generate equivalent or greater flow rates than existing rapid infusion devices. The present inventive device can be used with central lines, venous cut-down catheters, or peripheral IVs that nurses and paramedics can insert, therefore, it has potential application for use in ambulances, in the field, in emergency rooms, military applications, battlefield situations and the like.

The device can be used for blood transfusions imparting motion by a pressure change, i.e., it can add fluid to tubing which already contains the same or different fluid and thereby impart increased motion to the fluid already in the tubing without such fluid coming into contact with any other portion of the device, therefore any pump mechanism can be used. The present invention also has excellent potential for military applications. Current hyperinfusion devices have no place in the military/battlefield areas. Their cost, size, lack of efficiency and lack of qualified field personnel preclude use of prior art hyperinfusion devices in such a setting.

Therefore, the military has no access to hyperinfusion technology due to the size, cost and complexity of current devices. The present invention is small and portable. It can be sized to fit in a person's hand and can be powered by A.C. or D.C. current. If powered by D.C. current, standard batteries can be used, including rechargeable batteries. Preferably when the infuser of the present invention is used in the field or in military applications, it can be less than about 5 inches by about 5 inches by about 3 inches, however the size is dependent upon the components used.

In patients suffering blood loss, measuring the pressure in the large central veins, (central venous pressure or C.V.P.) assesses the efficacy of volume replacement. If the C.V.P. is low, the patient does not have adequate intravascular volume and thus further fluid resuscitation is necessary. A high C.V.P. is an indication of volume overload and can result in heart failure and pulmonary edema (or fluid) in the lungs. Presently, to measure C.V.P., a large catheter is placed in the patient's neck and connected to a pressure transducer which converts pressure changes into an electrical signal displayed on an oscilloscope-type monitor. Intensive care units and operating rooms are usually the only hospital areas capable of measuring C.V.P. In the ER setting, fluid administration is gauged empirically using only the patient's blood pressure and pulse to assess the adequacy of volume replacement. Hyperinfusion devices are best used while simultaneously monitoring C.V.P. The volume and rate of flow into the patient can then be quickly and accurately adjusted to sustain an adequate C.V.P. The hyperinfuser of the present invention can optionally infuse fluids and measure C.V.P. through a single central venous catheter. The small device not only rapidly infuses fluid and monitors C.V.P., but can adjust the flow rate automatically to achieve any C.V.P. the physician desires. The present invention not only insures the ideal infusion rate for any particular patient, but is an inexpensive alternative to large, expensive C.V.P. monitors and obviates the need to place a second venous catheter dedicated only to C.V.P. readings. The present invention can include a dial to set the desired C.V.P., a screen that displays the actual C.V.P., and a mechanism that stops the pump at pre-set time intervals in order to accurately measure the C.V.P. The operator need only select how many times per minute the pump should stop, read the C.V.P., and adjust the flow rate accordingly. A manual mode is provided to infuse at a simple fixed rate with a switch that will halt the pump and give the operator an instantaneous C.V.P. reading. An automated control means may be optionally used which maintains the C.V.P. within a preset range. The adjustable pump means responds to signals from the control means and increases or decreases the fluid pressure and/or flow rate in response thereto. Advantageously, the inventive device has an alarm indicating when the IV fluid bag approaches empty. The central venous pressure previously mentioned is measured by attaching directly into a vein within the chest. The present invention can also respond to pulmonary capillary wedge pressure, i.e., an output from a different machine, by having the separate machine provide information to the base unit. The pumping mechanism of the present invention optionally is adjustable based upon data received from any type of physiologic monitoring that indicates intervascular volume status, artery or vein pressure, urinary output, cardiac output and any type of bodily pressure measurement device. One such device determines the pulmonary capillary wedge pressure, an indirect measure of left ventricular filling pressure. Another device determines the urine output of the patient and the pumping mechanism responds to and is adjustable based upon this data. The present invention can also analyze and respond to various parameters which are indicated or set by the physician or technician.

The rapid infusion system is composed of two major portions. One portion includes permanent equipment, i.e., equipment which need not be sterilized and can be used over and over again, such as the pump motor and its related controls and optional equipment such as a C.V.P. monitor and related controls, optionally a heating element, conductive, convective, radiant, microwave, or other means of imparting heat to the fluid infused, and related controls and attachment means. The other portion includes the removable components of the system which may be disposable and/or semi-permanent equipment such as the pump and pump gears or rollers, which advantageously are reusable, and blood or fluid reservoir, valves and tubing, which advantageously are disposable.

The disclosed rapid infusion system is an adjustable mechanical pumping system for rapidly delivering blood and/or volume expanding fluids to a patient suffering from acute hypovolemia. The principle of operation of the disclosed invention is one of mechanically overcoming resistance. "Blood" is used herein to describe or refer to blood, blood components, and/or volume expanding fluids or colloids delivered by the system since not only blood, but any other desired fluid may be delivered by the system. "Reservoir" as used herein includes one or more standard IV bags or separate container(s) where such containers are more practical than an IV bag.

The subject invention pertains to a novel system for rapid intravenous infusion of a physiologic fluid, such as blood, which can include in combination a reservoir for the physiologic fluid having an inlet port for receiving the physiologic fluid and an outlet port for dispensing the physiologic fluid, an infusion pump to propel the physiologic fluid through the system, optional means for controlling the temperature of the physiologic fluid, optional means for filtering occlusive materials from the physiologic fluid, optional means for sensing the pressure of the physiologic fluid, means for infusing the physiologic fluid into a venous system and means for conveying the physiologic fluid to and from each of the components of the system.

In a preferred embodiment, the adjustable rapid infusion system comprises a reservoir that can have a capacity that can exceed several liters for holding a supply of physiologic fluid, the inventive infusion pump selected from known pumps, including, but not limited to the group consisting of gear pumps, turbine pumps, screw pumps, diaphragm pumps, centrifugal pumps, centripetal pumps, piston pumps, peristatic pumps, roller head occlusive pumps, nonocclusive centrifugal pumps and the like; optional portions such as a flow rate feed back means that can adjust the fluid flow rate responsive to inputs, a temperature controlling means; a filter to remove any occlusive material from the physiologic fluid; a sensor for detecting the presence of air, tube occlusion, or increased pressure in the physiologic fluid in conjunction with means for cutting off the flow in the conduit in response to a detected predetermined quantity of air, presence of an occlusion or increased pressure. The pump advantageously is infinitely adjustable and can provide fluid flow rates from about 40 cc/hour to about 2.5 l/minute. Optionally, the present rapid infusion system may employ two or more pumps depending upon the amount of fluid needed.

Optionally, the system may further include temperature sensors, if used in conjunction with the optional heater, at the output of the temperature controlling means for measuring and adjusting the physiologic temperature to maintain the temperature within acceptable limits. The system may also have readout means, which display fluid temperature, line pressure, fluid flow rate, total volume of fluid infused, and other parameters that imply the volume status of the patient.

The inventive system has a variable speed pump motor so that the amount of volume being pumped in can be increased merely by increasing the rpm of the motor. The reservoir may contain plural stages of filters and be provided with a plurality of inlets whereby volume from multiple sources can be fed into the reservoir to satisfy any high demand requirements of a patient. As set forth above, the system comprises a permanent portion and a removable and disposable portion. The removable portion can include any pumping means and components with which the fluid may come into contact.

Figure 1:
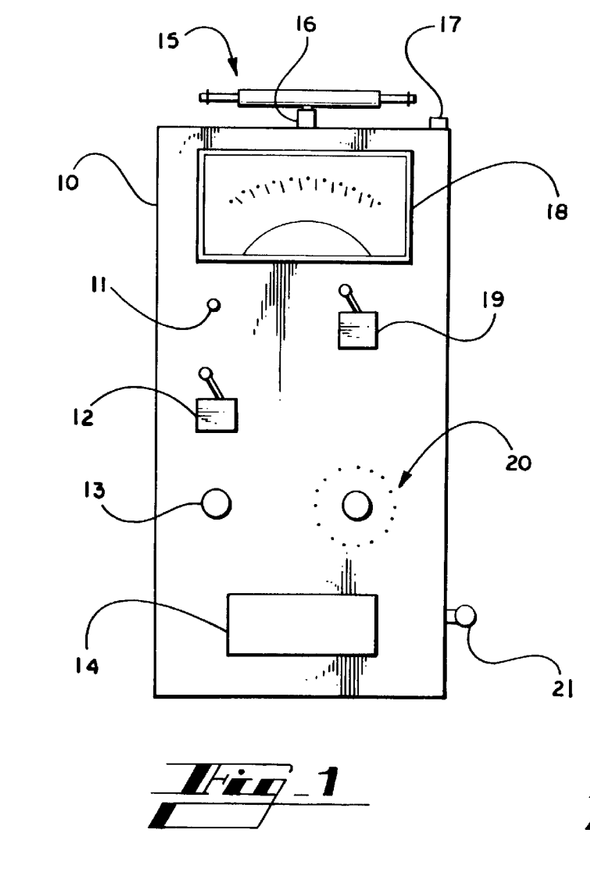
FIG. 1 is a front elevational view of the rapid infusion system.

Referring now in detail to FIG. 1, the rapid infusion device 10 of the present invention includes an on/off power switch 11, a C.V.P., or other bodily pressure measurement device for determining when the measured pressure is within or outside set parameters, a feedback mode on/off switch 12 for activating the measurement device, a variable flow rate control 13 for use when a bodily pressure measurement device is not being monitored and a liquid crystal display bodily pressure measurement readout 14. Pump mechanism 15 is driven by and removably connected to device 10 by attachment to shaft 16. Optionally, pump mechanism 15 may be recessed within device 10 so that it does not extend outside device 10. Device 10 also includes a C.V.P. data input jack 17, a fluid flow meter 18, an A.C./D.C. power selector switch 19, a bodily pressure measurement device setting 20 for use in the feedback mode and an external supply/charger port 21.

Figures 2, 3:
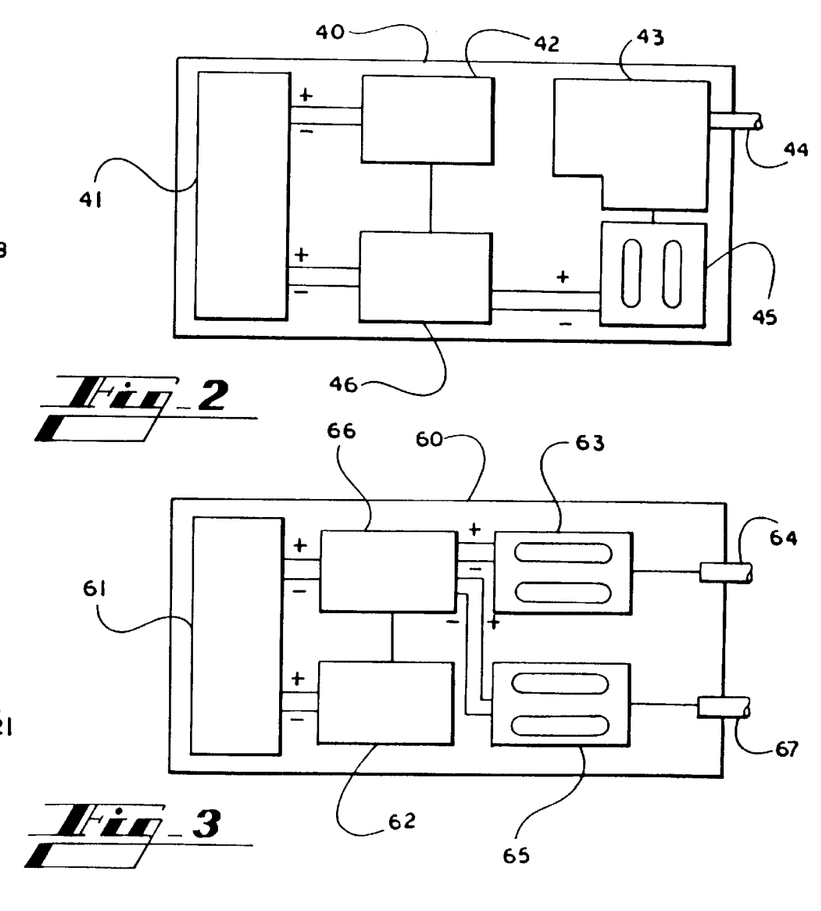
FIG. 2 is a schematic of one embodiment of the present invention.
FIG. 3 is a schematic of another embodiment of the present invention.

FIG. 2 is a schematic of one embodiment of the present invention wherein rapid infusion device 40 has a battery pack 41 connected to a central venous pressure feedback regulator 42. A drive gear box 43 is connected to a shaft 44 for driving a pump mechanism (not shown) and is driven by motor 45. Means, 46, to vary the resistance is connected to battery pack 41 and motor 45 and can vary the speed of motor 44 and thus the rotational speed input to gear box 43 and the pump mechanism. Gear box 43 may also include adjustable gearing to enable easily switching from a gear pump mechanism to a roller pump mechanism and vice-versa.

FIG. 3 is a schematic of another embodiment of the present invention having optional multiple pump mechanisms wherein rapid infusion device 60 has a battery pack 61, a bodily pressure measurement flow regulator 62, a motor 63 with shaft 64, and a motor 65 with shaft 67. A means, 66, to vary the resistance is connected to battery pack 61, regulator 62, motor 65 and motor 63, and can vary the speed of motors 63, 65, thereby varying the rotational speed input to the single or multiple pump mechanism(s) (not shown) which attaches to the shafts 64, 67.

Figure 4:
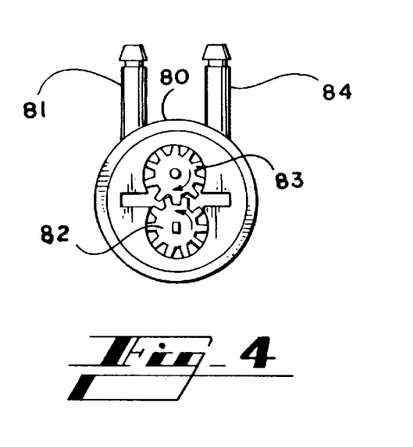
FIG. 4 is a sectional view of a pump mechanism used in one embodiment of the present invention.

FIG. 4 is a sectional view of one type of pump usable in an embodiment of the present invention. Gear pump 80 is attachable to shaft 16 of device 10 thereby driving pump means 82 and 83 and imparting motion to fluid received from a reservoir through opening 81 and exiting through opening 84.

Figure 5:
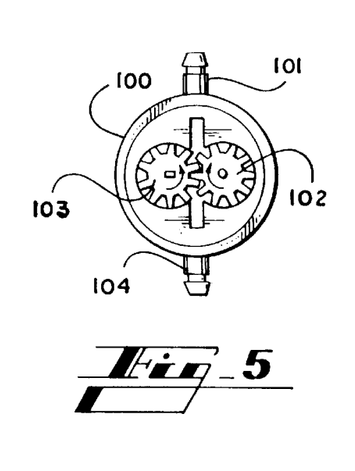
FIG. 5 is a sectional view of a pump mechanism used in another embodiment of the present invention.

FIG. 5 is a sectional view of one type of pump usable in another embodiment of the present invention wherein mechanism 100 is attachable to shaft 16 of device 10 thereby driving pump means 103 and 102 and imparting motion to a fluid from a reservoir received through opening 101 and exiting through opening 104. As can be seen the fluid goes through channels around the circumference of pump means 102 and 103 and exits through opening 104.

Figure 6:
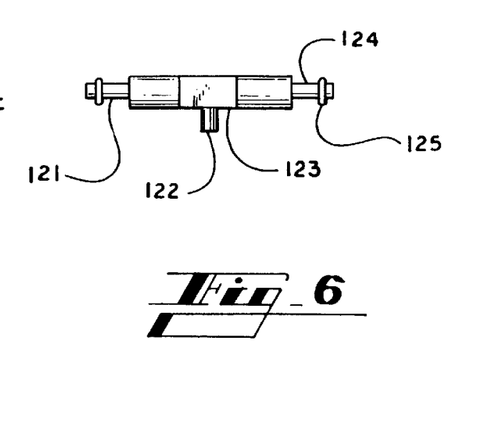
FIG. 6 is a side view of a pump mechanism showing the connections to the rapid infusion unit.

FIG. 6 is a side view of a pump mechanism usable with the present invention whereby shaft 122 is connected to shaft 16 of unit 10, thereby driving gear 123 which imparts motion to fluid received from a reservoir through opening 121 and exiting through opening 124. Annular shoulders 125 provide secure attachment to tubing or the like.

Figure 7:
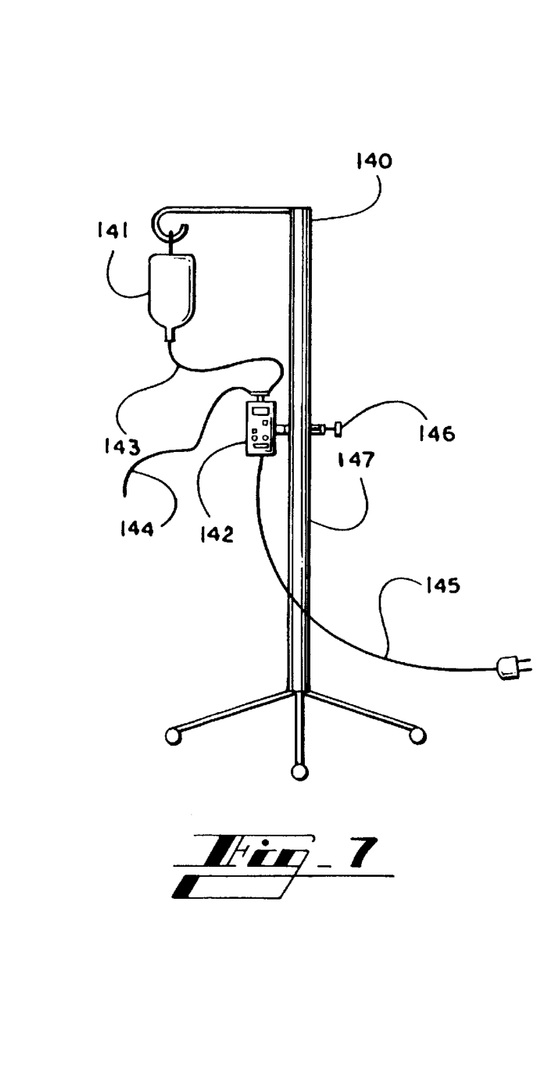
FIG. 7 is a frontal view showing an IV pole, fluid bag and the rapid infusion system of the present invention.

FIG. 7 is a typical IV arrangement 140 for hanging an IV bag 141 containing fluid which flows through tubing 143 to the rapid infusion device 142 of the present invention. Device 142 is attached to pole 147 by attachment means 146 and imparts motion to the fluid from bag 141 and directs it through tubing 144 to a patient. Device 142 may be powered by a battery or an external power source through cord 145.

Figure 8:
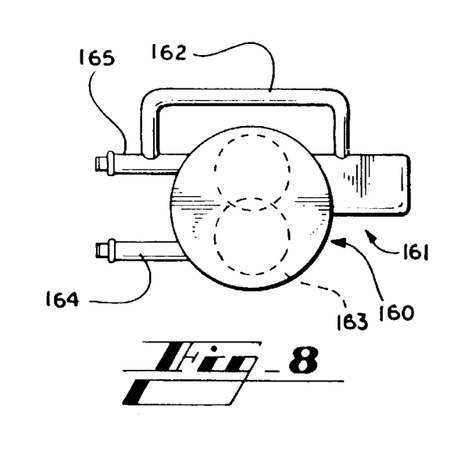
FIG. 8 is a frontal view of the present invention showing the optional C.V.P. monitoring apparatus.

FIG. 8 is a sectional view showing an optional C.V.P. monitoring system for the present invention. Pumping mechanism 160 contains a pressure probe 161 connected by a conduit 162 to the outlet 165 of the pumping mechanism. Fluid enters the pumping mechanism from a reservoir through inlet 164 whereby motion is imparted to the fluid by the pumping mechanism gears 163. The fluid pressure with the pump stopped is measured through conduit 165 and tubing 162 which communicates with pressure probe 161.

Figure 9:
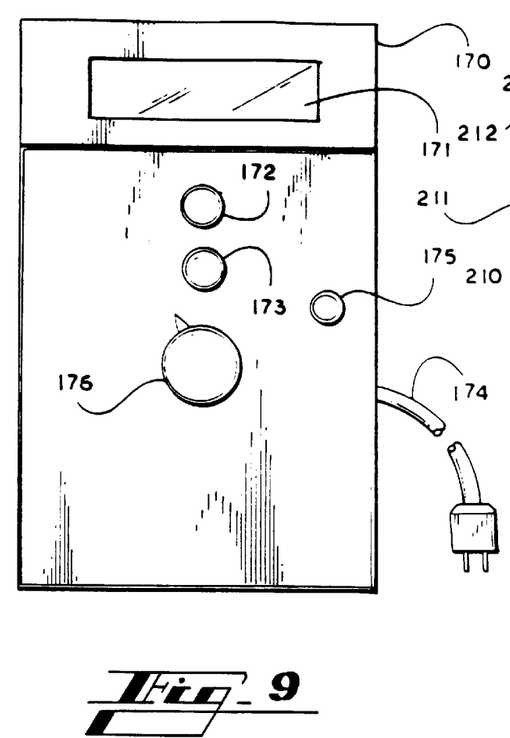
FIG. 9 is a frontal view of another embodiment of the present invention.

FIG. 9 is a front view of the motor drive unit of one embodiment of the present invention. Flow adjuster 176 variably adjusts motive force to the drive unit resulting in fluid flow rates to a patient from about 40 cc/hour to about 2.5 l/minute. Switch 175 selects either AC or DC power to the unit. Plug 174 connects to an AC source where one is provided. Flow range selection switch 173 adjusts the motive force to the drive unit thereby providing for either high flow (500 cc/hour to 2.5 l/minute) and low flow, including maintenance flow, (40 cc/hour to 500 cc/hour). Switch 172 is a power on/off switch. Meter 171 indicates fluid flow when the unit is in operation. Housing 170 encases the unit. In one embodiment the removable portion (or unit) can be either a plastic, metal, composite, or the like device with the tubing therein. The plastic device is intended for disposal after use and the tubing may be a permanent portion of the housing. Another embodiment is more semi-permanent that may be attached to the top of the motor drive unit allowing one to flip open the top of the pump mechanism and replace the tubing, enabling anyone with a minimum amount of training to operate the mechanism. Advantageously the present invention encompasses different types of pump attachments, semi-permanent, i.e. which may include a pumping mechanism having a flip open top, i.e. the top can be opened and the tubing as well as other parts of the mechanism that come into contact with the fluid can be removed and replaced. This portion of the top may be releasably attached by known means such as hinges, snaps, latches, and the like.

Figure 10:
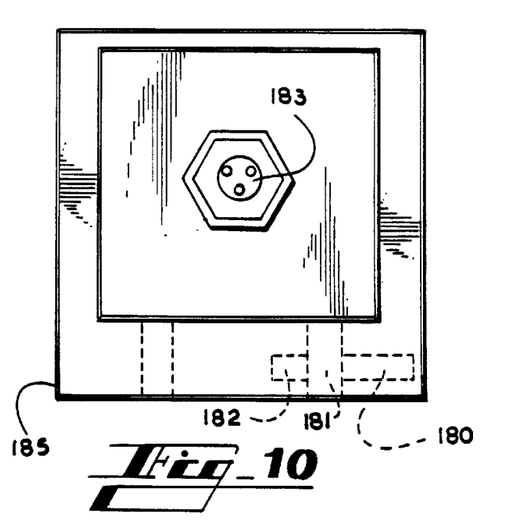
FIG. 10 is a top view of the embodiment shown in FIG. 9.

Referring to FIG. 10, there is provided air detector transmitter 180 and air detector receiver 182 or any other means for determining the presence of air in the fluid before the fluid is directed to a patient. Trough 181 is provided for a length of tubing or a coupling device, preferably a leur-lock or other tubing coupling means (not shown) including a portion through which flow, temperature, etc. can be measured. Drive shaft coupler 183 mates with coupler 222 (shown in FIG. 14) which is attached to top housing 185. A flow probe or sensor determines the fluid flow rate and may be ultrasonic or other known types of sensors.

Figure 11:
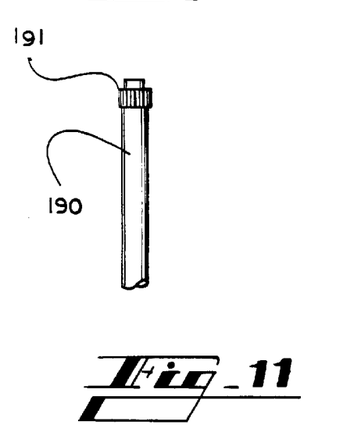
FIG. 11 is a fragmentary view depicting one connection means usable in the present invention.

FIG. 11 depicts IV tubing 190 having a male leur-lock coupling device with connector 191.

Figure 12:
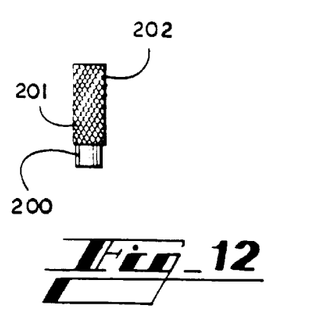
FIG. 12 is a fragmentary view depicting another connection means usable with the present invention.
Figure 13:
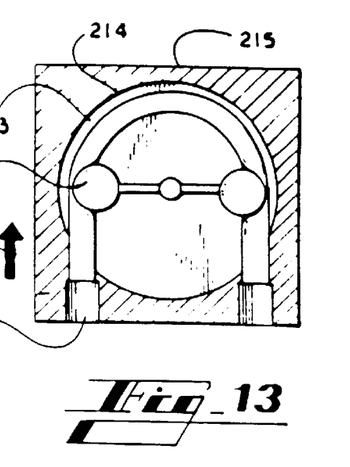
FIG. 13 is a sectional top view of a variable speed portable roller pump embodiment of the present invention.

FIG. 12 shows removable female leur-lock coupling 200 with interchangeable leur-lock adaptor 201 having threads 202 which screws into the unit 215 at lock receptacle 210 (shown in FIG. 13). This allows easy replacement with apparatus of the same size as that removed or with a different size, resulting in different flow rates and capacities.

FIG. 13 shows a roller mechanism contained in housing 215 which has a threaded leur-lock receptacle 210 and indicates a fluid flow direction of 211. Roller 212 compresses collapsible tube 213 against compression surface 214, thereby imparting motion to the fluid within tube 213. Tube 213 which may be removable, disposable and replaceable with another length of tube in one embodiment, may be a permanent portion in another embodiment. Housing 215 is removable and it and the components therein other than tube 213 are reusable.

Figure 14:
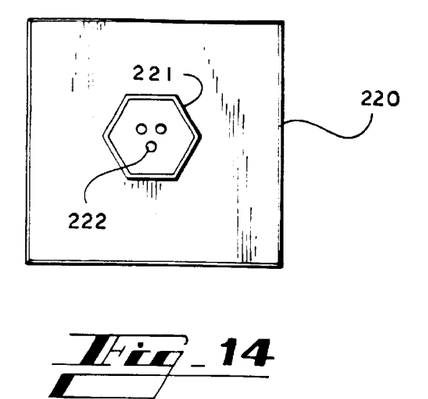
FIG. 14 is a bottom view of the embodiment shown in FIG. 13.

FIG. 14 shows bottom housing 220 having a connector 221 for attachment to the base unit and motor drive shaft coupler 222 which imparts motion to the pump mechanism. FIG. 14 shows detachable housing 220, having connector 221 shown as a hexagonal friction coupler, for attachment to the base unit and motor driver shaft coupler 222. The hexagonal coupler frictionally locks it onto the base unit and the teeth from the drive shaft (not shown) are separate entities that interdigitate. The hexagonal coupler is a fixed unit and may be made of molded plastic. Although the preferred embodiment of attaching the roller pump to the base unit is the described hexagonal friction coupling system, the present invention is not limited to that embodiment since other coupling means known in the art are included.

Figure 15:
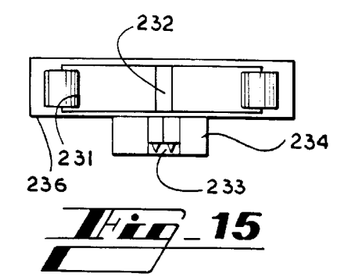
FIG. 15 is a sectional side view of the embodiment depicted in FIG. 13.

FIG. 15 is a sectional side view of the roller mechanism shown in FIG. 13 and depicts housing 236 having drive coupler 233 in association with friction coupler 234 which imparts motion to roller 231 about pivot point 232, thereby imparting motion to the fluid.

Figure 16:
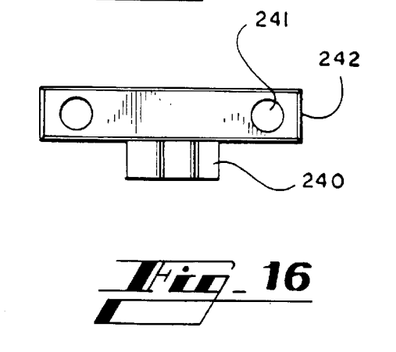
FIG. 16 is a side view of the embodiment depicted in FIG. 13.

FIG. 16 is a side view of the roller mechanism shown in FIG. 13 and depicts housing 242 showing fluid outflow receptacle 241 and friction coupler 240 associated therewith.

Figure 17:
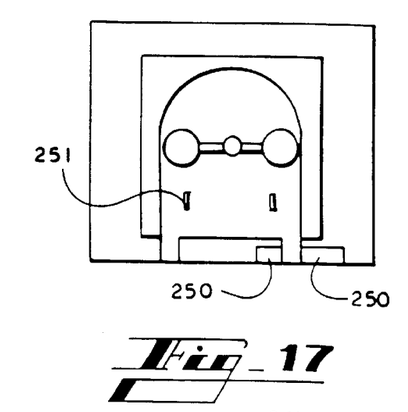
FIG. 17 is a top view of the drive unit with a permanent pump head.

FIG. 17 is a top view of one embodiment of the present invention showing motor drive unit 251 and bubble detector 250 for detecting air in the fluid before transmitting the fluid to a patient, which is advantageously semi-permanent and can be completely disposable or in which only the tubing and/or fluid temperature adjustment means may be disposable.

Figure 18:
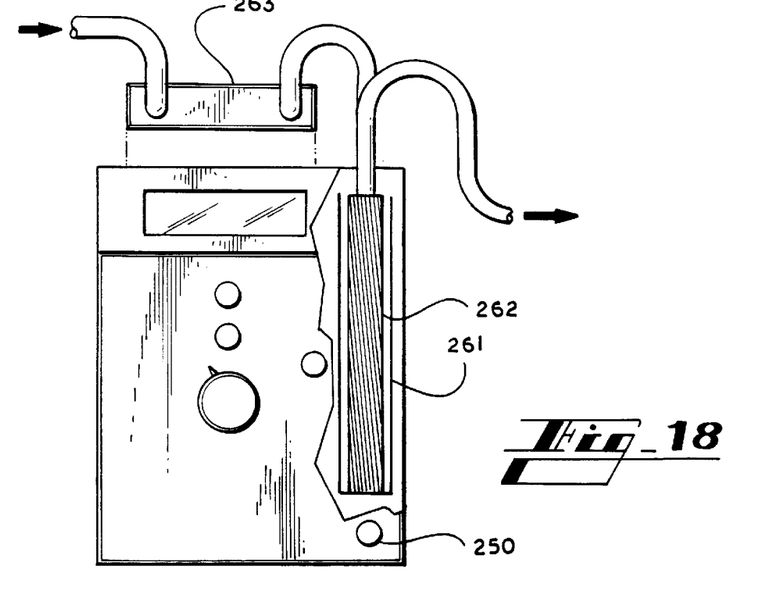
FIG. 18 is a side view of the permanent pump having a flip top for easy access, showing disposable tubing.

FIG. 18 is a side view partly in section showing the present invention having fluid temperature adjustment unit 261, depicted with optional fluid cassette 262 having increased surface area to impart desired temperature adjustment to the fluid, for heating or cooling, and on-off switch 260 for controlling the unit. The pump head contains releasably attached top 263, shown in side view, which provides easy access to replace the disposable tubing in the pump mechanism. Temperature adjustment unit 261 is adjacent to fluid cassette 262. Optionally unit 261 may be contained within the infusion device near fluid cassette 262. The fluid enters temperature adjustment unit 261 from the pump mechanism, travels through fluid channels, the temperature is adjusted to be within set parameters, exits the unit and is transmitted to a patient. The fluid channels may be formed within the unit, may be contained within a removable portion such as a cassette insertable into the unit, or may be contained in a separate unit and attached to the pump mechanism fluid output tube.

Figures 19, 20, 21, 22:
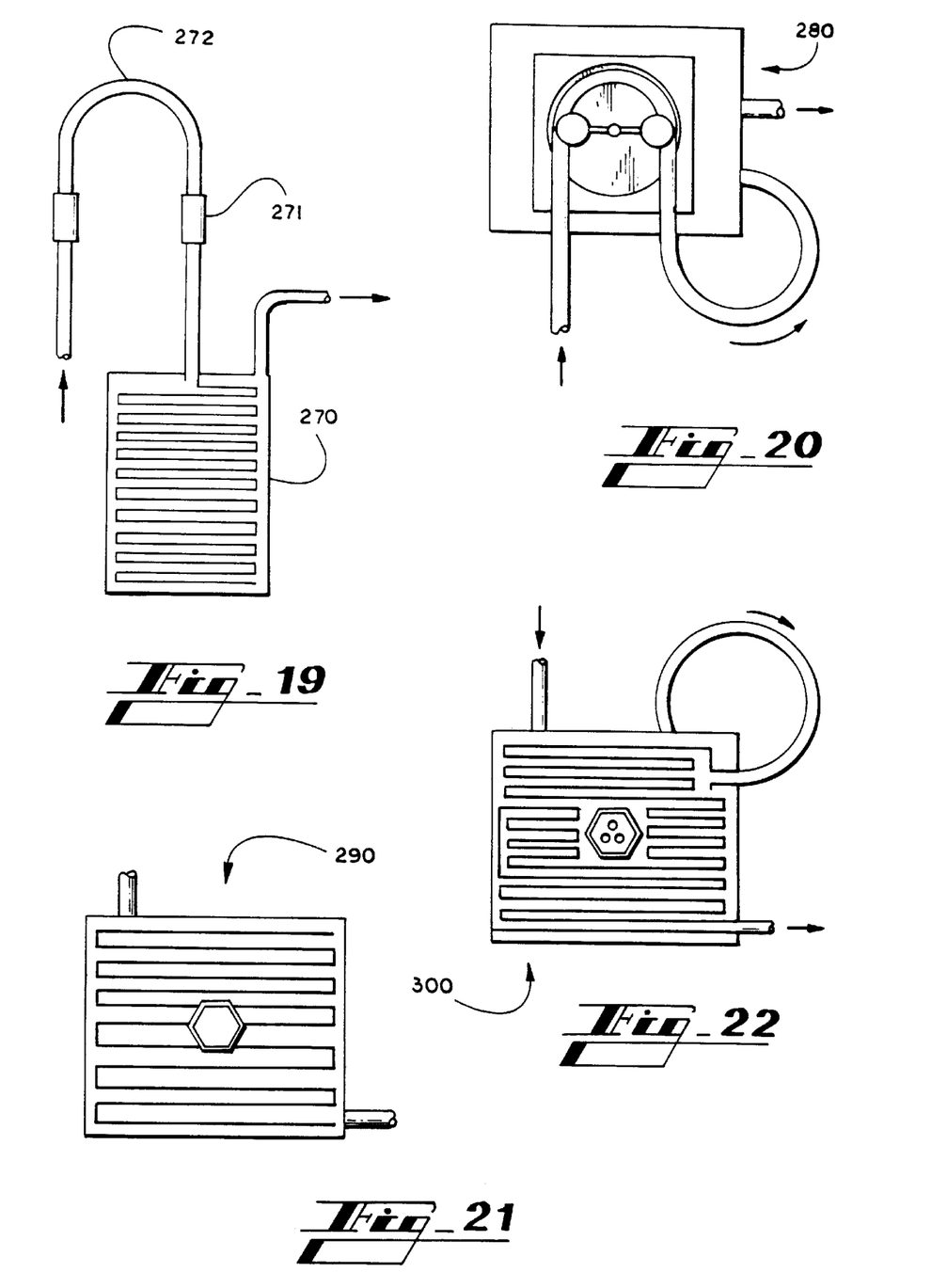
FIG. 19 is a side view of a removable fluid channel cassette.
FIG. 20 is a top view of a disposable pump head unit showing the channels therein.
FIG. 21 is a sectioned top view of a motor drive unit of the present invention showing optional heating coils.
FIG. 22 is a sectioned bottom view of the disposable pump head of the present invention showing the fluid channels.

FIG. 19 depicts the removable tubing apparatus, advantageously useable with the semi-permanent pump mechanism, which can be completely disposable or in which only the tubing and/or the fluid cassette may be disposable, which preferably is manufactured of heat conducting material, showing cassette having fluid channels 270. Compressible tubing portion 272 is acted upon by the roller pump to impart motion to the fluid within the tubing which is held in place by guides 271. The present invention optionally may include heat exchange means associated with the cassette and/or separately with the tubing.

FIG. 20 depicts disposable head unit 280 in section showing the action of the roller pump on a length of tubing. In this embodiment unit 280 is capable of attachment to the top of the infusion device shown in FIG. 18.

FIG. 21 is a top view in section of the motor drive unit showing optional temperature adjustment heating coils 290 which may be used instead of, or in addition to, the temperature adjustment unit 261 shown in FIG. 18.

FIG. 22 is a bottom view in section of a disposable pump head which comes in contact with the heating means of FIG. 21 showing optional fluid temperature adjustment channels 300, preferably covered by a heat conductive material. This optional unit may be employed instead of, or in addition to, the temperature adjustment unit 261 shown in FIG. 18. The disposable pump head of this embodiment is attachable to the top of the infusion device shown in FIG. 18.

As indicated previously, the materials of construction of the present invention are those normally used for medical applications. In one embodiment of the present invention, the apparatus is portable, thereby dictating small size and lightweight. Where weight is a major factor, the housing and roller pump mechanism are manufactured of a lightweight material. Advantageously the housing and pump mechanism are comprised of a plastic material.

Although the major use of the present invention is to infuse quantities of blood into a patient, it can also be used to infuse other fluids such as a dye into a vein or artery for imaging purposes. The present invention can also be used as an irrigator, to clean wounds during laparoscopic surgery and in regular surgical procedures where any common irrigator is used.

Unlike standard or traditional methods of intravenous fluid administration, the inventive rapid infusion system can provide continuous total replacement of adult human blood volume through any sort of hemorrhage, for an indefinite period of time and can rapidly regulate fluid temperature with minimal increase in resistance to flow, easily and rapidly administer massive quantities of blood to a single patient during a single operation, administer physiologic fluid maintained at a predetermined temperature at flow rates in excess of 2.5 l per minute, and permit simultaneous display and control of fluid temperature, flow rate, line pressure, and total volume of physiologic fluid administered. The present invention allows for two ways to achieve the wide flow ranges listed, including, but not limited to: by changing the pump gears and by changing the pump motor. These changes may be accomplished automatically by switching means activated by various fluid and/or bodily sensors. The system also is portable and able to be quickly and easily used in an emergency situation or by emergency personnel in the field. The blood delivered by the system can include clotting factors and can infuse an infinite amount of blood over an indefinite period of time based on the pump mechanism employed, the tubing sizes, etc., employed. The system can also include a heating apparatus which imparts heat to the fluid flowing through a tube or through a channel within the apparatus, thereby controlling the fluid temperature.

If desired the present invention can consist of multiple pumps infusing blood or the like to a patient through multiple catheters, thereby providing such fluids in volumes to the patient which are far in excess of that possible by present infusers.

While the invention has been described in its preferred embodiment, it is to be understood that the words which have been used are words of description rather than limitation and that changes may be made within the purview of the appended claims without departing from the scope or spirit of the invention.

What is claimed is:

1. An infusion pump for delivering fluid from a fluid reservoir to a patient through a fluid conduit, comprising:

a pump head that imparts motion to fluid in a fluid conduit; and a driver that imparts motion to the pump head;

wherein the pump head further includes temperature adjustment channels so that the fluid can be heated as it travels through the pump head and wherein the pump head is removably attached to the driver.

2. The infusion pump of claim 1, wherein the temperature adjustment channels are covered by a heat conductive material.

3. The infusion pump of claim 1, wherein the driver is contained within a motor drive unit and the motor drive unit contains temperature adjustment heating coils that can apply heat to the temperature adjustment channels of the pump head.

4. The infusion pump of claim 3, wherein the pump head is removably attached to the driver and the temperature adjustment heating coils on the motor drive unit contact the temperature adjustment channels of the pump head when the pump head is attached to the driver.

5. The infusion pump of claim 1, further comprising a fluid conduit removable from the pump head.

6. The infusion pump of claim 1, wherein the driver includes a motor having a drive shaft attached thereto and the pump head removably attaches to the driver shaft.

7. The infusion pump of claim 1, wherein the pump includes a coupler that transfers motion from the drive shaft to the pump head.

8. The infusion pump of claim 7, wherein the coupler is a hexagonal friction coupling system.

9. The infusion pump of claim 1, wherein the pump head includes a friction coupler and the driver includes a mating friction coupler.

10. The infusion pump of claim 1, wherein the pump head is a gear pump head, roller pump head, or centrifugal pump head.

11. The infusion pump of claim 1, wherein the pump head is a roller pump head.

12. The infusion pump of claim 1, wherein the pump head has a receptacle for removably attaching a fluid conduit.

13. The infusion pump of claim 1, further comprising a fluid conduit in the receptacle.

* * * * *